United States Patent [19]

Jordan

[11] Patent Number: 5,389,129
[45] Date of Patent: Feb. 14, 1995

[54] WAX POLISH COMPOSITION

[75] Inventor: Martin P. Jordan, Orpington, England

[73] Assignee: Berwind Pharmaceutical Services, Inc., West Point, Pa.

[21] Appl. No.: 889,775

[22] Filed: May 28, 1992

[30] Foreign Application Priority Data

May 29, 1991 [GB] United Kingdom ............... 9111514

[51] Int. Cl.$^6$ ................................................. A61K 9/42
[52] U.S. Cl. ................................ 106/10; 426/305; 424/476; 106/3; 106/271
[58] Field of Search ............... 106/3, 10, 271; 426/305; 424/476

[56] References Cited

U.S. PATENT DOCUMENTS

| | | | |
|---|---|---|---|
| 2,598,666 | 6/1952 | Sesso et al. | 106/271 |
| 3,438,797 | 4/1969 | Biddle | 424/476 |
| 4,043,829 | 8/1977 | Ratledge et al. | 106/271 |
| 4,055,433 | 10/1977 | Morones | 106/10 |
| 4,183,757 | 1/1980 | Groszek et al. | 106/271 |
| 4,793,850 | 12/1988 | Koester et al. | 106/271 |
| 4,797,288 | 1/1989 | Sharma et al. | 427/476 |
| 5,023,108 | 6/1991 | Bagaria et al. | 427/476 |

*Primary Examiner*—Mark L. Bell
*Assistant Examiner*—C. M. Bonner
*Attorney, Agent, or Firm*—John F. A. Earley; John F. A. Earley, III

[57] ABSTRACT

A polish composition for pharmaceutical tablets, food products and confectionery pieces comprises beeswax, carnauba wax, water and emulsifier. A polish composition for pharmaceutical tablet, food products and confectionery pieces comprises wax, water and an emulsifier with an HLB value of about 16 to about 17.

20 Claims, No Drawings

WAX POLISH COMPOSITION

The present invention relates to a wax polish composition, such as a wax polish composition for a pharmaceutical tablet or a confectionery piece.

Conventional wax polish compositions are solutions of wax in an organic solvent such as carbon tetrachloride or ether. However, these solvents give rise to processing problems in the application of the polish to pharmaceutical tablets or confectionery pieces. For example, the removal of waste organic solvent vapour formed during the polishing process from exhaust air streams is very expensive, and an increasing number of countries do not allow vapours of organic solvents to be vented directly into the atmosphere. Further, many organic solvents are dangerous fire hazards and toxicity hazards to process workers. Moreover, inadvertent over-use of such wax solutions may spoil the product by the adhesion of excess wax to the surface.

If conventional wax polishing is performed in the presence of water, the surface of the tablet or piece to which the wax polish has been applied is usually subjected to over-washing which causes spoiling of the tablet's surface.

It has been proposed in U.S. Pat. No. 3,438,797, issued Apr. 15, 1969 to Biddle, to apply an unpolished wax undercoating to a sugar coated tablet using a wax in water emulsion. After the undercoating has been applied, the tablet is imprinted with ink indicia, given a protective outer coating of a suitable transparent material, such as, for example, carnauba wax, beeswax, or a combination thereof, and polished to impart a pharmaceutically acceptable finish.

The present invention provides in a first aspect a polish composition comprising beeswax, carnauba wax, water and an emulsifier.

The emulsifier preferably has a hydrophile-lipophile balance value ("HLB value") of about 16 to about 17.

The present invention further provides in a second aspect a polish composition comprising wax, water and an emulsifying agent which has an HLB value between about 16 and about 17.

The polish compositions of the invention find particular application in the polishing of pharmaceuticals, to form polished tablets, and of food/confectionery pieces.

The emulsifier is effective and suitable for dispersing the components of the emulsion. Preferred emulsifiers are: polyoxyethylene 20 sorbitan monolaurate, commercially available under the trade names Polysorbate 20 and Tween 20; polyoxyethylene 40 stearate; and blends thereof.

When the step of applying the polish compositions of the invention is accomplished using conventional coating methods other than spraying, the emulsifier preferably comprises at least 5% by weight of the composition. Using non-spraying coating methods, the range for the emulsifier is between 5% and about 18.15% by weight of the composition, with the preferred range being between 5% and 8% by weight of the composition.

Optimally, the polish compositions of the present invention may contain a preservative, preferably in an amount of from 0.15% to 0.75% w/w when non-spraying coating methods are used to apply the polish compositions. Sorbic acid is a preferred preservative, preferably in an amount of 0.2% w/w when non-spraying coating methods are used. Other preservatives, active in the range pH 3.5 to 5.5 and acceptable for food/pharmaceutical use, may be used.

When non-spraying coating methods are used to apply the polish compositions, the total wax content of the polish composition is preferably from 33 to 50% by weight of the composition, still more preferably from 35 to 48% by weight of the composition. If the proportion of wax in the polish composition exceeds 50%, the composition may become too viscous to be mangeable. When non-spraying coating methods are used, for polish compositions of the present invention which comprise two waxes, the amount of each wax component is preferably from 16.5 to 25% by weight of the composition. In compositions according to the first aspect of the invention beeswax and carnauba wax are preferably present in substantially equal amounts.

When a conventional coating method other than spraying is used to apply the polish compositions of the invention to substrates (e.g. pharmaceutical tablets and food/confectionery pieces), a suitable range of water is about 45.38% to about 60.00% w/w.

The most preferred composition of the present invention is:

| | |
|---|---|
| wax | 41.60% |
| water | 51.95% |
| emulsifier | 6.25% |
| preservative | 0.20% |

The polish compostion of the invention may be made by heating the wax, or waxes, and water together, preferably to around 80° C., to melt the wax, and cooling the mixture while stirring until a stable emulsion is formed, typically at a temperature of about 60° C. The emulsifier and any other ingredients may be added before or after heating.

Alternatively, melted wax or waxes with the emulsifier are added to hot water, and the mixture cooled with stirring to form a stable emulsion.

The invention will now be described further with reference to the following examples:

EXAMPLE 1

The following components are gradually heated in a large beaker until the waxes melt:

| | |
|---|---|
| 208 g | beeswax |
| 208 g | carnauba wax |
| 519.5 g | purified water |
| 62.5 g | Polysorbate 20 |
| 2.0 g | sorbic acid |
| 1000.00 | |

The source of heat is then removed and the mixture is stirred continously using a high sheer stirrer with an emulsifying head, such as a silverson stirrer, until the mixture cools to around 60° C. The mixture is allowed to cool to ambient temperature. The product is a stable wax-in-water emulsion.

EXAMPLE 2

Example 1 is repeated except that the emulsifier Polysorbate 20 is replaced by 62.5 g of the emulsifier polyoxyethylene 40 stearate. The product is a stable wax-in-water emulsion.

EXAMPLE 3

Example 1 is repeated using 228.8 g of beeswax, 228.8 g carnauba wax, 477.9 g water, 62.5 g Polysorbate 20, and 2.0 g sorbic acid. A stable wax-in-water emulsion is produced.

EXAMPLE 4

Example 1 is repeated using 80 g Polysorbate 20 and 502 g water instead of 62.5 g Polysorbate 20 and 519.5 g of water. The product is a stable wax-in-water emulsion.

EXAMPLE 5

Beeswax and carnauba wax in the amounts in Example 1 are melted together with 62.5 g of Polysorbate 20. 519.5 g of water with 2.0 g sorbic acid are heated separately to around 80° C. The hot solution of sorbic acid is added to the molten wax/emulsifier mixture with stirring using the high sheer stirrer of Example 1. The mixture is continuously stirred while. cooling until the temperature drops to 60° C. On cooling to ambient temperture a stable wax-in-water emulsion is produced.

EXAMPLES 6-16

The following Examples 6 to 17, which show different formulations of the invention, further illustrate the invention. In each Example 6 to 17 a stable wax-in-water emulsion is made using the procedure of Example 1. Tween 20 is an emulsifier made by ICI Specialties, Manchester, United Kingdom.

EXAMPLE 6

| Component | g | % |
| --- | --- | --- |
| beeswax | 60.00 | 19.29 |
| carnauba wax | 60.00 | 19.29 |
| purified water | 150.00 | 48.22 |
| Tween 20 | 40.50 | 13.02 |
| sorbic acid | 0.55 | 0.18 |

EXAMPLE 7

| Component | g | % |
| --- | --- | --- |
| beeswax | 60.00 | 18.15 |
| carnauba wax | 60.00 | 18.15 |
| purified water | 150.00 | 45.38 |
| Tween 20 | 60.00 | 18.15 |
| sorbic acid | 0.55 | 0.17 |

EXAMPLE 8

| Component | g | % |
| --- | --- | --- |
| beeswax | 60.00 | 20.62 |
| carnauba wax | 60.00 | 20.62 |
| purified water | 150.00 | 51.56 |
| Tween 20 | 20.40 | 7.01 |
| sorbic acid | 0.55 | 0.19 |

EXAMPLE 9

| Component | g | % |
| --- | --- | --- |
| beeswax | 60.00 | 20.40 |
| carnauba wax | 60.00 | 20.40 |
| purified water | 150.00 | 51..01 |
| Tween 20 | —23.52 | 8.00 |
| sorbic acid | 0.55 | 0.19 |

EXAMPLE 10

| Component | g | % |
| --- | --- | --- |
| beeswax | 60.00 | 21.06 |
| carnauba wax | 60.00 | 21.06 |
| purified water | 150.00 | 52.66 |
| Tween 20 | 14.30 | 5.02 |
| sorbic acid | 0.55 | 0.19 |

EXAMPLE 11

| Component | g | % |
| --- | --- | --- |
| beeswax | 60.00 | 20.84 |
| carnauba wax | 60.00 | 20.84 |
| purified water | 150.00 | 52.11 |
| Tween 20 | 17.30 | 6.01 |
| sorbic acid | 0.55 | 0.19 |

EXAMPLE 12

| Component | g | % |
| --- | --- | --- |
| beeswax | 66.00 | 21.96 |
| carnauba wax | 66.00 | 21.96 |
| purified water | 150.00 | 49.90 |
| Tween 20 | 18.03 | 6.00 |
| sorbic acid | 0.55 | 0.18 |

EXAMPLE 13

| Component | g | % |
| --- | --- | --- |
| beeswax | 54.00 | 19.52 |
| carnauba wax | 54.00 | 19.52 |
| purified water | 150.00 | 54.23 |
| Tween 20 | —18.03 | 6.52 |
| sorbic acid | 0.55 | 0.20 |

EXAMPLE 14

| Component | g | % |
| --- | --- | --- |
| beeswax | 60.00 | 17.31 |
| carnauba wax | 60.00 | 17.31 |
| purified water | 208.00 | 60.02 |
| Tween 20 | 18.00 | 5.19 |
| sorbic acid | 0.55 | 0.16 |

EXAMPLE 15

| Component | g | % |
| --- | --- | --- |
| beeswax | 60.00 | 20.69 |
| carnauba wax | 60.00 | 20.69 |
| purified water | 150.00 | 51.72 |
| Tween 20 | 18.00 | 6.21 |
| sorbic acid | 2.02 | 0.70 |

EXAMPLE 16

| Component | g | % |
| --- | --- | --- |
| beeswax | 60.00 | 20.80 |
| carnauba wax | 60.00 | 20.80 |
| purified water | 150.00 | 52.01 |
| Tween 20 | 18.00 | 6.24 |
| sorbic acid | 0.42 | 0.15 |

EXAMPLE 17

| Component | g | % |
| --- | --- | --- |
| beeswax | 208.00 | 13.58 |
| carnauba wax | 208.00 | 13.58 |
| purified water | −1052.00 | 68.63 |
| Tween 20 | 62.50 | 4.08 |
| sorbic acid | 2.0 | 0.13 |

The polish compositions of the present invention may be used to coat tablets with a layer of wax to impart a gloss to the tablet surface, and any of the conventional tablet coating methods may be used, including conventional round or hexagonal sugar coating pans, canvas-lined pans and side-vented coating pans. Further, the inventive composition invention may be applied to pharmaceutical tablets and food/confectionery items using a simple ladling technique, in which a sufficient volume of the composition to cover the surface of the tablets or food/confectionery items being polished is poured over those tablets or food/confectionery items as they are being agitated by rotation of the aforementioned equipment. Drying air and exhaust ventilation may be employed to promote drying of the composition.

The composition may be used as a single application or it may be preferably divided into two or more applications with intervening drying steps. Once an even layer of wax has been deposited, the tablets or food/confectionery items continue to be rolled in the equipment until the required gloss develops.

As an alternative to the ladling technique, the composition may be applied to the tablets and food/confectionery items in the form of a fine spray, using either air-atomised or airless technology, in the same type of coating equipment as specified above. The composition may be diluted with water to facilitate spraying. A typical diluted formula is represented by Example 17, in which the formula of Example 1 is diluted by the addition of extra water. The inventive composition of Example 17 may be diluted even further with water than the formula of Example 17, but this would serve no useful purpose as the application time would then be excessively long due to the very dilute nature of the formula. In general, the inventive polish compositions, including each of the formulae of Examples 1 to 16, may be diluted as much as desired to meet the conditions needed for coating by spraying. However, as the polish composition becomes more dilute, spraying times increase. When the wax composition is applied by spraying, continuous drying air and exhaust ventilation may be used. Spraying is continued until an even layer of wax is deposited and then rotation continued until the required gloss develops.

Pharmaceutical tablets and food/confectionery items which are traditionally subjected to a wax polishing process, generally have water soluable surfaces. Without careful formulation, an aqueous polishing agent tends to dissolve the existing surface with resultant deleterious effects on the finished product appearance and possibly, stability. The present invention overcomes these problems by binding the water to the wax until is it lost by evaporation in the polishing pan.

The polish compositions of the present invention are applied to tablets to give a wax layer which is polishable without damage to the tablets surface.

The polish compositions of the present invention may be applied to any sugar coated tablet or confectionery piece.

The polish compositions of the present invention are not destroyed by repeated freezing and thawing. This is an advantage for manufacturers of coated tablets in locations where temperatures are often below freezing.

I claim:

1. A polish composition for coating pharmaceutical tablets and food/confectionery items to impart a gloss thereto, consisting essentially of 16.5 to 25% by weight beeswax and 16.5 to 25% by weight carnauba wax, 45 to 60% by weight of water, and at least 5% by weight of an emulsifier, the emulsifier having an HLB value of about 16 to about 17.

2. A polish composition according to claim 1 in which the emulsifier is polyoxyethylene 20 sorbitan monolaurate or polyoxyethylene 40 stearate.

3. The polish composition of claim 1, the emulsifier being present in an amount of from 5% to 18.15% by weight of the composition.

4. The polish composition of claim 1, the emulsifier being present in an amount of from 5% to 8% by weight of the composition.

5. The polish composition of claim 1, further including 0.15 to 0.75% by weight of a preservative.

6. The polish composition of claim 5, the preservative being sorbic acid.

7. The polish composition of claim 1, the beeswax and the carnauba wax being present in a total amount from 35 to 48% by weight of the composition.

8. The polish composition of claim 1, the beeswax and carnauba wax being present in substantially equal amounts.

9. A polish composition for coating pharmaceutical tablets and food/confectionery items to impart a gloss thereto, consisting essentially of 20.80% w/w beeswax, 20.80% w/w carnauba wax, 51.95% w/w water, 6.25% w/w emulsifier, and 0.20% w/w preservative, the emulsifier having an HLB value of about 16 to about 17,
the emulsifier being polyoxyethylene 20 sorbitan monolaurate or polyoxyethylene 40 stearate, and
the preservative being sorbic acid.

10. A method of coating pharmaceutical tablet substrates and food/confectionery substrates, with a layer of wax to impart a gloss thereto, consisting essentially of the steps of adding 33 to 50% by weight of beeswax and/or carnauba wax to 45–60% by weight of a solvent consisting essentially of water,
heating the wax and solvent until the wax has melted,
adding at least 5% by weight of an emulsifier to the melted wax and solvent,
cooling and stirring the wax, solvent, and emulsifier until the temperature drops to about 60° C. or less to obtain a polish composition, applying an effective amount of the polish composition onto each substrate to form a coating on each substrate, drying the coating on each substrate, and buffing the coating on each substrate to impart a gloss thereto.

11. The method of claim 10, the wax being a combination of beeswax and carnauba wax.

12. The method of claim 10, the emulsifier having an HLB value of about 16 to about 17.

13. The method of claim 10, the emulsifier being polyoxyethylene 20 sorbitan monolaurate or polyoxyethylene 40 stearate.

14. The method of claim 10, further including adding 0.15 to 0.75% by weight of a preservative to the polish composition.

15. The method of claim 14, the preservative being sorbic acid.

16. The method of claim 10, the emulsifier being in a range from 5% to about 18% by weight of the composition.

17. The method of claim 16, further including adding a preservative to the polish composition, the preservative being in a range from about 0.15% to about 0.75% by weight of the composition.

18. The method of claim 10, the wax being a combination of beeswax and carnauba wax, the waxes being present in substantially equal amounts.

19. The method of claim 13, the beeswax being present in an amount from 16.5 to 25% by weight of the composition and the carnauba wax being present in an amount from 16.5 to 25% by weight of the composition.

20. The method of claim 19, the beeswax and the carnauba wax being present in substantially equal amounts to one another.

* * * * *